United States Patent
Vikso-Nielsen et al.

(10) Patent No.: US 9,040,275 B2
(45) Date of Patent: May 26, 2015

(54) LACCASE FOR DETOXIFICATION OF FEED PRODUCTS

(75) Inventors: Anders Vikso-Nielsen, Slangerup (DK); Birthe Hauerbach Sorensen, Frederiksberg (DK)

(73) Assignee: Novozymes A/S, Bagsvaerd (DK)

( * ) Notice: Subject to any disclaimer, the term of this patent is extended or adjusted under 35 U.S.C. 154(b) by 825 days.

(21) Appl. No.: 12/333,414

(22) Filed: Dec. 12, 2008

(65) Prior Publication Data

US 2009/0155415 A1    Jun. 18, 2009

Related U.S. Application Data

(60) Provisional application No. 61/014,882, filed on Dec. 19, 2007.

(30) Foreign Application Priority Data

Dec. 14, 2007 (EP) .................................... 07150032

(51) Int. Cl.
| | |
|---|---|
| *C12N 9/02* | (2006.01) |
| *A23K 3/00* | (2006.01) |
| *C12P 7/00* | (2006.01) |
| *C12P 1/00* | (2006.01) |
| *A23K 1/06* | (2006.01) |
| *A23K 1/165* | (2006.01) |
| *A23K 1/18* | (2006.01) |
| *A23L 1/015* | (2006.01) |

(52) U.S. Cl.
CPC ................ *C12P 1/00* (2013.01); *C12N 9/0061* (2013.01); *A23K 1/06* (2013.01); *A23K 1/1656* (2013.01); *A23K 1/184* (2013.01); *A23L 1/0153* (2013.01)

(58) Field of Classification Search
CPC ... C12N 9/0061; A23K 1/006; A23K 1/1656; C12P 1/00
See application file for complete search history.

(56) References Cited

U.S. PATENT DOCUMENTS

| | | | |
|---|---|---|---|
| 2003/0073239 | A1 | 4/2003 | Karlovsky et al. |
| 2005/0142254 | A1 | 6/2005 | Yabe et al. |
| 2007/0292579 | A1 | 12/2007 | Schatzmayr et al. |
| 2008/0305521 | A1 | 12/2008 | Alves et al. |

FOREIGN PATENT DOCUMENTS

| | | |
|---|---|---|
| CA | 2192983 | 5/1996 |
| CN | 1657611 | 8/2005 |
| EP | 0981953 A2 | 3/2000 |
| EP | 1780270 A1 | 5/2007 |
| JP | 2002153257 | 5/2002 |
| WO | 99/23887 A1 | 5/1999 |
| WO | WO 2005/073381 | 8/2005 |
| WO | 2007/054034 A1 | 5/2007 |
| WO | WO 2007/133263 | 11/2007 |

OTHER PUBLICATIONS

Branden et al. Introduction to Protein Structure, Garland Publishing Inc., New York, p. 247, 1991.*
Jingwen, Feed Review, vol. 12, pp. 23-25 (2006).
Yaver et al., Genbank Accession No. AAC41686 (1996).
Brodhagen et al., Molecular Plant Pathology, vol. 7, No. 4, pp. 285-301 (2006).
Liu et al., Food and Chemical Toxicology, vol. 36, pp. 563-574 (1998).
Albert et al., Dissertation presented for the Degree of Doctor of Philosophy at the University of Stellenbosch entitled "Microbial Degradation of Mycotoxins"(Apr. 2007).

* cited by examiner

*Primary Examiner* — Yong Pak
(74) *Attorney, Agent, or Firm* — Elias Lambiris

(57) ABSTRACT

The present invention relates to a method for detoxification of feed products contaminated by the mycotoxin zearalenone.

20 Claims, No Drawings

SEQUENCE LISTING

```
<160> NUMBER OF SEQ ID NOS: 3

<210> SEQ ID NO 1
<211> LENGTH: 620
<212> TYPE: PRT
<213> ORGANISM: Myceliophthora thermophila
<220> FEATURE:
<221> NAME/KEY: mat_peptide
<222> LOCATION: (1)..(620)

<400> SEQUENCE: 1

Met Lys Ser Phe Ile Ser Ala Ala Thr Leu Leu Val Gly Ile Leu Thr
1               5                   10                  15

Pro Ser Val Ala Ala Ala Pro Pro Ser Thr Pro Glu Gln Arg Asp Leu
            20                  25                  30

Leu Val Pro Ile Thr Glu Arg Glu Ala Ala Val Lys Ala Arg Gln
        35                  40                  45
```

-continued

```
Gln Ser Cys Asn Thr Pro Ser Asn Arg Ala Cys Trp Thr Asp Gly Tyr
     50                  55                  60
Asp Ile Asn Thr Asp Tyr Glu Val Asp Ser Pro Asp Thr Gly Val Val
 65              70                  75                      80
Arg Pro Tyr Thr Leu Thr Leu Thr Glu Val Asp Asn Trp Thr Gly Pro
                 85                  90                  95
Asp Gly Val Val Lys Glu Lys Val Met Leu Val Asn Asn Ser Ile Ile
                100                 105                 110
Gly Pro Thr Ile Phe Ala Asp Trp Gly Asp Thr Ile Gln Val Thr Val
             115                 120                 125
Ile Asn Asn Leu Glu Thr Asn Gly Thr Ser Ile His Trp His Gly Leu
130                 135                 140
His Gln Lys Gly Thr Asn Leu His Asp Gly Ala Asn Gly Ile Thr Glu
145                 150                 155                 160
Cys Pro Ile Pro Pro Lys Gly Arg Lys Val Tyr Arg Phe Lys Ala
             165                 170                 175
Gln Gln Tyr Gly Thr Ser Trp Tyr His Ser His Phe Ser Ala Gln Tyr
             180                 185                 190
Gly Asn Gly Val Val Gly Ala Ile Gln Ile Asn Gly Pro Ala Ser Leu
         195                 200                 205
Pro Tyr Asp Thr Asp Leu Gly Val Phe Pro Ile Ser Asp Tyr Tyr Tyr
     210                 215                 220
Ser Ser Ala Asp Glu Leu Val Glu Leu Thr Lys Asn Ser Gly Ala Pro
225                 230                 235                 240
Phe Ser Asp Asn Val Leu Phe Asn Gly Thr Ala Lys His Pro Glu Thr
                245                 250                 255
Gly Glu Gly Glu Tyr Ala Asn Val Thr Leu Thr Pro Gly Arg Arg His
             260                 265                 270
Arg Leu Arg Leu Ile Asn Thr Ser Val Glu Asn His Phe Gln Val Ser
         275                 280                 285
Leu Val Asn His Thr Met Cys Ile Ile Ala Ala Asp Met Val Pro Val
     290                 295                 300
Asn Ala Met Thr Val Asp Ser Leu Phe Leu Gly Val Gly Gln Arg Tyr
305                 310                 315                 320
Asp Val Val Ile Glu Ala Asn Arg Thr Pro Gly Asn Tyr Trp Phe Asn
                325                 330                 335
Val Thr Phe Gly Gly Leu Leu Cys Gly Gly Ser Arg Asn Pro Tyr
             340                 345                 350
Pro Ala Ala Ile Phe His Tyr Ala Gly Ala Pro Gly Gly Pro Pro Thr
         355                 360                 365
Asp Glu Gly Lys Ala Pro Val Asp His Asn Cys Leu Asp Leu Pro Asn
     370                 375                 380
Leu Lys Pro Val Val Ala Arg Asp Val Pro Leu Ser Gly Phe Ala Lys
385                 390                 395                 400
Arg Ala Asp Asn Thr Leu Asp Val Thr Leu Asp Thr Thr Gly Thr Pro
                405                 410                 415
Leu Phe Val Trp Lys Val Asn Gly Ser Ala Ile Asn Ile Asp Trp Gly
             420                 425                 430
Arg Ala Val Val Asp Tyr Val Leu Thr Gln Asn Thr Ser Phe Pro Pro
         435                 440                 445
Gly Tyr Asn Ile Val Glu Val Asn Gly Ala Asp Gln Trp Ser Tyr Trp
     450                 455                 460
```

```
Leu Ile Glu Asn Asp Pro Gly Ala Pro Phe Thr Leu Pro His Pro Met
465                 470                 475                 480

His Leu His Gly His Asp Phe Tyr Val Leu Gly Arg Ser Pro Asp Glu
            485                 490                 495

Ser Pro Ala Ser Asn Glu Arg His Val Phe Asp Pro Ala Arg Asp Ala
        500                 505                 510

Gly Leu Leu Ser Gly Ala Asn Pro Val Arg Arg Asp Val Ser Met Leu
        515                 520                 525

Pro Ala Phe Gly Trp Val Val Leu Ser Phe Arg Ala Asp Asn Pro Gly
        530                 535                 540

Ala Trp Leu Phe His Cys His Ile Ala Trp His Val Ser Gly Gly Leu
545                 550                 555                 560

Gly Val Val Tyr Leu Glu Arg Ala Asp Asp Leu Arg Gly Ala Val Ser
            565                 570                 575

Asp Ala Asp Ala Asp Leu Asp Arg Leu Cys Ala Asp Trp Arg Arg
            580                 585                 590

Tyr Trp Pro Thr Asn Pro Tyr Pro Lys Ser Asp Ser Gly Leu Lys His
            595                 600                 605

Arg Trp Val Glu Glu Gly Glu Trp Leu Val Lys Ala
            610                 615                 620

<210> SEQ ID NO 2
<211> LENGTH: 520
<212> TYPE: PRT
<213> ORGANISM: Polyporus pinsitus
<220> FEATURE:
<221> NAME/KEY: mat_peptide
<222> LOCATION: (1)..(520)

<400> SEQUENCE: 2

Met Ser Arg Phe His Ser Leu Leu Ala Phe Val Val Ala Ser Leu Thr
1               5                   10                  15

Ala Val Ala His Ala Gly Ile Gly Pro Val Ala Asp Leu Thr Ile Thr
            20                  25                  30

Asn Ala Ala Val Ser Pro Asp Gly Phe Ser Arg Gln Ala Val Val Val
        35                  40                  45

Asn Gly Gly Thr Pro Gly Pro Leu Ile Thr Gly Asn Met Gly Asp Arg
50                  55                  60

Phe Gln Leu Asn Val Ile Asp Asn Leu Thr Asn His Thr Met Val Lys
65                  70                  75                  80

Ser Thr Ser Ile His Trp His Gly Phe Phe Gln Lys Gly Thr Asn Trp
            85                  90                  95

Ala Asp Gly Pro Ala Phe Ile Asn Gln Cys Pro Ile Ser Ser Gly His
            100                 105                 110

Ser Phe Leu Tyr Asp Phe Gln Val Pro Asp Gln Ala Gly Thr Phe Trp
        115                 120                 125

Tyr His Ser His Leu Ser Thr Gln Tyr Cys Asp Gly Leu Arg Gly Pro
130                 135                 140

Phe Val Val Tyr Asp Pro Asn Asp Pro Ala Ala Asp Leu Tyr Asp Val
145                 150                 155                 160

Asp Asn Asp Asp Thr Val Ile Thr Leu Val Asp Trp Tyr His Val Ala
            165                 170                 175

Ala Lys Leu Gly Pro Ala Phe Pro Leu Gly Ala Asp Ala Thr Leu Ile
        180                 185                 190

Asn Gly Lys Gly Arg Ser Pro Ser Thr Thr Thr Ala Asp Leu Ser Val
        195                 200                 205
```

-continued

Ile Ser Val Thr Pro Gly Lys Arg Tyr Arg Phe Arg Leu Val Ser Leu
    210                 215                 220

Ser Cys Asp Pro Asn Tyr Thr Phe Ser Ile Asp Gly His Asn Met Thr
225                 230                 235                 240

Ile Ile Glu Thr Asp Ser Ile Asn Thr Ala Pro Leu Val Val Asp Ser
                245                 250                 255

Ile Gln Ile Phe Ala Ala Gln Arg Tyr Ser Phe Val Leu Glu Ala Asn
            260                 265                 270

Gln Ala Val Asp Asn Tyr Trp Ile Arg Ala Asn Pro Asn Phe Gly Asn
        275                 280                 285

Val Gly Phe Thr Gly Gly Ile Asn Ser Ala Ile Leu Arg Tyr Asp Gly
    290                 295                 300

Ala Ala Ala Val Glu Pro Thr Thr Thr Gln Thr Thr Ser Thr Ala Pro
305                 310                 315                 320

Leu Asn Glu Val Asn Leu His Pro Leu Val Thr Thr Ala Val Pro Gly
                325                 330                 335

Ser Pro Val Ala Gly Gly Val Asp Leu Ala Ile Asn Met Ala Phe Asn
            340                 345                 350

Phe Asn Gly Thr Asn Phe Phe Ile Asn Gly Thr Ser Phe Thr Pro Pro
        355                 360                 365

Thr Val Pro Val Leu Leu Gln Ile Ile Ser Gly Ala Gln Asn Ala Gln
    370                 375                 380

Asp Leu Leu Pro Ser Gly Ser Val Tyr Ser Leu Pro Ser Asn Ala Asp
385                 390                 395                 400

Ile Glu Ile Ser Phe Pro Ala Thr Ala Ala Pro Gly Ala Pro His
                405                 410                 415

Pro Phe His Leu His Gly His Ala Phe Ala Val Val Arg Ser Ala Gly
            420                 425                 430

Ser Thr Val Tyr Asn Tyr Asp Asn Pro Ile Phe Arg Asp Val Val Ser
        435                 440                 445

Thr Gly Thr Pro Ala Ala Gly Asp Asn Val Thr Ile Arg Phe Arg Thr
    450                 455                 460

Asp Asn Pro Gly Pro Trp Phe Leu His Cys His Ile Asp Phe His Leu
465                 470                 475                 480

Glu Ala Gly Phe Ala Val Val Phe Ala Glu Asp Ile Pro Asp Val Ala
                485                 490                 495

Ser Ala Asn Pro Val Pro Gln Ala Trp Ser Asp Leu Cys Pro Thr Tyr
            500                 505                 510

Asp Ala Leu Asp Pro Ser Asp Gln
            515                 520

<210> SEQ ID NO 3
<211> LENGTH: 343
<212> TYPE: PRT
<213> ORGANISM: Streptomyces coelicolor
<220> FEATURE:
<221> NAME/KEY: mat_peptide
<222> LOCATION: (1)..(343)

<400> SEQUENCE: 3

Met Asp Arg Arg Gly Phe Asn Arg Arg Val Leu Leu Gly Gly Ala Ala
1               5                   10                  15

Ala Ala Thr Ser Leu Ser Ile Ala Pro Glu Val Ala Gly Ala Ala Pro
            20                  25                  30

Ala Ala Lys Gly Ile Thr Ala Arg Thr Ala Pro Ala Gly Gly Glu Val

```
                         35                  40                  45
Arg His Leu Lys Met Tyr Ala Glu Lys Leu Ala Asp Gly Gln Met Gly
         50                  55                  60

Tyr Gly Phe Glu Lys Gly Lys Ala Ser Val Pro Gly Pro Leu Ile Glu
65                  70                  75                   80

Val Asn Glu Gly Asp Thr Leu His Ile Glu Phe Thr Asn Thr Met Asp
                    85                  90                  95

Val Arg Ala Ser Leu His Val His Gly Leu Asp Tyr Glu Ile Ser Ser
                100                 105                 110

Asp Gly Thr Ala Met Asn Lys Ser Asp Val Glu Pro Gly Gly Thr Arg
                115                 120                 125

Thr Tyr Thr Trp Arg Thr His Lys Pro Gly Arg Arg Asp Asp Gly Thr
130                 135                 140

Trp Arg Pro Gly Ser Ala Gly Tyr Trp His Tyr His Asp His Val Val
145                 150                 155                 160

Gly Thr Glu His Gly Thr Gly Gly Ile Arg Asn Gly Leu Tyr Gly Pro
                165                 170                 175

Val Ile Val Arg Arg Lys Gly Asp Val Leu Pro Asp Ala Thr His Thr
                180                 185                 190

Ile Val Phe Asn Asp Met Thr Ile Asn Asn Arg Lys Pro His Thr Gly
                195                 200                 205

Pro Asp Phe Glu Ala Thr Val Gly Asp Arg Val Glu Ile Val Met Ile
                210                 215                 220

Thr His Gly Glu Tyr Tyr His Thr Phe His Met His Gly His Arg Trp
225                 230                 235                 240

Ala Asp Asn Arg Thr Gly Ile Leu Thr Gly Pro Asp Asp Pro Ser Arg
                245                 250                 255

Val Ile Asp Asn Lys Ile Thr Gly Pro Ala Asp Ser Phe Gly Phe Gln
                260                 265                 270

Ile Ile Ala Gly Glu Gly Val Gly Ala Gly Ala Trp Met Tyr His Cys
                275                 280                 285

His Val Gln Ser His Ser Asp Met Gly Met Val Gly Leu Phe Leu Val
                290                 295                 300

Lys Lys Pro Asp Gly Thr Ile Pro Gly Tyr Glu Pro His Glu His Gly
305                 310                 315                 320

Gly Ala Thr Ala Lys Ser Gly Glu Ser Gly Glu Pro Thr Gly Gly Ala
                325                 330                 335

Ala Ala His Glu His Glu His
                340
```

LACCASE FOR DETOXIFICATION OF FEED PRODUCTS

CROSS-REFERENCE TO RELATED APPLICATIONS

This application claims priority or the benefit under 35 U.S.C. 119 of European application no. 07150032.6 filed Dec. 14, 2007 and U.S. provisional application No. 61/014,882 filed Dec. 19, 2007, the contents of which are fully incorporated herein by reference.

REFERENCE TO SEQUENCE LISTING

This application contains a Sequence Listing in computer readable form. The computer readable form is incorporated herein by reference.

FIELD OF THE INVENTION

The present invention relates to a method for detoxification of feed products contaminated by the mycotoxin zearalenone.

BACKGROUND OF THE INVENTION

Several plant pathogenic and/or post-harvest *Fusarium* species on cereals produce toxic substances of considerable concern to livestock and poultry producers, e.g., deoxynivalenol, T-2 toxin, HT-2 toxin, diacetoxyscirpenol and zearalenone.

Zearalenone is found worldwide in a number of cereal crops, such as maize, barley, oats, wheat, rye, rice, millet and sorghum. Zearalenone production does not seem to occur in significant amounts prior to harvest, but under proper environmental conditions, it is readily produced on corn and small grains in storage.

When cereal grain is used in ethanol production and the starch is consumed the zearalenone is concentrated in the fermentation by-products, e.g., in the distiller's dried grain. The contents of zearalenone in the fermentation by-products may be increased three-fold relative to the cereal grain.

The toxin is heat-stable, and it is not destroyed by long storage, roasting, or by the addition of propionic acid or mold retardants.

Despite their structural dissimilarity to the steriodal estrogens, zearalenone and several of its derivatives possess estrogenic activity. Zearalenone undergoes a folding such that hydroxyl or potential hydroxyl groups become appropriately orientated to facilitate binding to tissue receptors that normally bind estrogens.

Zearalenone is the primary toxin causing infertility, abortion or other breeding problems, especially in swine. The symptoms are especially severe in prepubertal gilts including enlarged mammae, swelling of uterus and vulva, and atrophy of the ovaries. In severe cases, prolapse of the vulva and rectum may occur. Boars exhibit enlarged mammae and atrophied testes.

Zearalenone is present in the meat from animals feeding on contaminated grain as well as in bread baked from contaminated wheat. While cases of poisoning of humans are rare there is concern about the effect of the long term exposure of humans to such an estrogenic activity.

Inactivation of mycotoxins, including zearalenone, using epoxidase or lactonase is disclosed in WO 96/12414.

There is a need for further methods of detoxification of animal feed products, e.g., such as fermentation by-products, including distiller's wet and dried grain, contaminated by the mycotoxin zearalenone.

SUMMARY OF THE INVENTION

The inventors of the present invention have discovered that a mycotoxin in a feed product can be degraded into non-toxic substances by treating the feed product with a laccase. Accordingly, in a first aspect the invention provides a process for degrading a mycotoxin in a feed product which process comprises treating said feed product with a laccase. The mycotoxin is preferably zearalenone.

In a second aspect the invention provides a use of a laccase for degrading a mycotoxin.

DETAILED DESCRIPTION OF THE INVENTION

Zearalenone

In the context of this invention the term "zearalenone" comprises the mycotoxin zearalenone produced from certain *Fusarium* sp. The IUPAC name is (4S,12E)-15,17-dihydroxy-4-methyl-3-oxabicyclo[12.4.0]octadeca-12,15,17,19-tetraene-2,8-dione. The term "zearalenone" also comprises any derivative of zearalenone which comprises one or more hydroxyl groups susceptible for modification by a laccase.

Animal Feed Products

The term "animal" includes all animals, including human beings. Examples of animals are cattle, (including but not limited to cows and calves); mono-gastric animals, e.g., pigs or swine (including, but not limited to, piglets, growing pigs, and sows); poultry such as turkeys and chicken (including but not limited to broiler chicks, layers); and fish (including but not limited to salmon).

The term "feed" or "feed product" means any compound, preparation, mixture, or composition suitable for, or intended for intake by an animal.

The feed product may be a product which apart from an unwanted level of zearalenone is suitable for consumption by an animal. The feed product can also be a product suspected of comprising an unwanted level of zearalenone, and/or a product having an unknown level of zearalenone, including products not comprising a detectable level of zearalenone.

Preferably the feed product is a grain based product. Preferably the grain based product comprises cereal(s), e.g., one or more of corn, wheat, barley, rye, rice, sorghum and millet. In one embodiment, the feed product may, e.g., be derived solely from cereal(s), and in another embodiment partly from legumes, e.g., from soybean, and partly from cereals. The grain based product may comprise whole or milled grain, e.g., wet or dry milled grain, including grain based product comprising fractions of wet or dry milled grain, e.g., gluten, protein, starch, and/or oil fractions. Also preferred are products comprising by-product from brewing and/or fermentation processes, e.g., spent grains. Spent grains are the by-products from the production of alcoholic beverages and ethanol fuels. Brewers' spent grain (BSG) is the residue of beer making in breweries, which use malted barley as the major raw material. Distiller's spent grain (DSG) is the product left in distilleries after alcohol is removed by distillation from the fermented grains such as corn, wheat, barley, rice, and rye. Distiller's spent grain is also known as distiller's grain. Wet distiller's grain (WDG) is dried to produce dried distiller's grain (DDG) which is used primarily as animal feed.

Laccases

In the context of this invention the term "laccases" include enzymes comprised by the enzyme classification E.C. 1.10.3.2.

Preferred are the below mentioned enzymes, especially recombinant and/or substantially purified enzymes.

Preferably, the laccase employed is derived from a strain of *Polyporus* sp., in particular a strain of *Polyporus pinisitus* or *Polyporus versicolor*, or a strain of *Myceliophthera* sp., e.g., *M. thermophila* or a strain of *Rhizoctonia* sp., in particular a strain of *Rhizoctonia praticola* or *Rhizoctonia solani*, or a strain of a *Rhus* sp., in particular *Rhus vemicifera*.

In specific embodiments of the invention the oxidoreductase is a *Polyporus* sp. laccase especially the *Polyporus pinisitus* laccase (also called *Trametes villosa* laccase) described in WO 96/00290 or a *Myceliophthera* sp. laccase especially the *Myceliophthera thermophila* laccase described in WO 95/33836.

Further, the laccase may be a *Scytalidium* sp. laccase, such as the *S. thermophilium* laccase described in WO 95/33837 or a *Pyricularia* sp. laccase, such as the *Pyricularia oryzae* laccase which can be purchased from SIGMA under the trade name SIGMA no. L5510, or a *Coprinus* sp. laccase, such as a *C. cinereus* laccase, especially a *C. cinereus* IFO 30116 laccase, or a *Rhizoctonia* sp. laccase, such as a *R. solani* laccase, especially the neutral *R. solani* laccase described WO 95/07988 having a pH optimum in the range from 6.0 to 8.5.

The laccase may also be derived from a fungus such as *Aspergillus, Botrytis, Collybia, Coriolus* sp., e.g., *C. hirsitus* (JP 2-238885), *Fomes, Lentinus, Neurospora, Phlebia*, e.g., *P. radiata* (WO 92/01046), *Pleurotus*, or *Podospora*.

In preferred embodiments the laccase is a laccase from *Myceliophthora thermophila* (MtL) having the amino acid sequence deposited as GENESEQP: AAR88500 and shown herein as SEQ ID NO: 1, a laccase from *Polyporus pinsitus* (PpL) having the amino acid sequence deposited as UNI-PROT: Q99044 and shown herein as SEQ ID NO: 2, a laccase from *Streptomyces coelicolor* ScL having the amino acid sequence deposited as SWISSPROT: Q9XAL8 and shown herein as SEQ ID NO: 3, or a laccase having an amino acid sequence homologous to any of these sequences.

The laccase must be present in the medium to be detoxified in effective amounts. Preferably the laccase is present in concentrations of 0.01-100 mg enzyme protein per kg dry matter, preferably 0.1-10 mg enzyme protein per kg dry matter, or more preferably 1-5 mg enzyme protein per kg dry matter.

The Mediator

In an embodiment a mediator acting as electron donors for the laccase is used together with the laccase. The mediator should be present in the medium to be detoxified in effective amounts.

Various mediators are known; see, e.g., WO 94/12620, WO 94/12621, WO 95/01626, WO 96/00179 and WO 99/23887. Mediators therein are hereby incorporated by reference.

Preferred for the invention is a mediator selected from Methylsyringate (MES), Phenothiazine-10-propionicacid (PPT), N-(4-cyanophenyl)acetohydroxamic acid (NCPA), acetosyringone, syringaldehyde, p-coumaric acid, 2,2'-Azinobis(3-ethylbenzthiazoline-6-sulfonate), 1-hydroxybenzotriazole, 2,4-pentanedione, and phenothiazine.

Said mediators are commercially available or can be made by methods known to the art.

The Medium

In an embodiment the laccase is degrading the zearalenone in a medium comprising the feed product. The medium is preferably aqueous and may be a liquid, a paste or a slurry. To form a suitable medium water may be added to the feed product. The laccase and the mediator may be comprised, either separately or together, in solid or liquid formulations suitable for application to said medium.

In a embodiment the laccase is degrading the zearalenone to an extent whereby the content of zearalenone per kg dry matter feed product is reduced to less than 50%, less than 60%, less than 70%, preferably less than 80%, more preferably less than 85%, yet more preferably less than 90%, and most preferably less than 95% of the initial amount.

The detoxifixabon efficiency of the invention depends on, e.g., availability of oxygen, pH, temperature and buffer of the medium. For example, the treatment may take place at a pH-value at which the relative activity of the actual laccase is at least 50, or 60, or 70, or 80 or 90%. Likewise, for example, the treatment may take place at a temperature at which the relative activity of the actual laccase is at least 50, or 60, or 70, or 80 or 90%. The relative activity is calculated relative to the activity at the pH value where the highest activity is observed.

Oxygen in the Medium

The source of oxygen required by the laccase may be oxygen from the atmosphere or an oxygen precursor for in situ production of oxygen. Oxygen from the atmosphere will usually be present in sufficient quantity. If more $O_2$ is needed, additional oxygen may be added, e.g., as pressurized atmospheric air or as pure pressurized oxygen.

pH in the Medium

Depending, inter alia, on the characteristics of the laccase and the mediator employed, the pH in the medium employed should normally be in the range of 5-11, preferably in the range 6-10, e.g., 6.5-8.5.

Temperature in the Medium

Preferably a reaction temperature is applied which is dose to the optimum temperature for the laccase. In numerous embodiments of the invention, temperatures in the range of 10-65° C., more preferably 30-50° C., should be employed.

Treatment Duration

The duration of treatment depends, inter alia, on the treatment type, the type of item to be treated, the properties of the medium, e.g., temperature and pH and the type and amounts of enzyme and mediator employed.

The enzymatic reaction is continued until the desired result is achieved, following which it may or may not be stopped by inactivating the enzyme, e.g., by a heat-treatment step.

For detoxification purposes treatment times in the range of 1 minute to 1 week may be employed. In many cases a treatment time in the range of 6 to 48 hours will be suitable.

Identity

The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLO-SUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Homologous Sequence

The term "homologous sequence" is defined as a predicted protein that gives an E value (or expectancy score) of less than 0.001 in a tfasty search (Pearson, W. R., 1999, in *Bioinformatics Methods and Protocols*, S. Misener and S. A. Krawetz, ed., pp. 185-219) with a specified sequence.

The term "homologous sequence" may also be defined as a sequence that has a degree of identity at least 75%, at least 80%, at least 85%, at least 90%, at least 95%, at least 97%, at least 98%, at least 99%, or even 100%, to a specified sequence.

EXAMPLES

Example 1

Materials and Methods

Enzymes

A laccase from *Myceliophthora thermophila* (MtL) having the amino acid sequence shown herein as SEQ ID NO: 1.

A laccase from *Polyporus pinsitus* (PpL) having the amino acid sequence shown herein as SEQ ID NO: 2.

A laccase from *Streptomyces coelicolor* (ScL) having the amino acid sequence shown herein as SEQ ID NO: 3.

Mediators

Methylsyringate (MeS)

Phenothiazine-10-propionicacid (PPT)

Assay:

Reactions were performed in 300 microL volumes in eppendorf tubes comprising zearalenone 30 microM, mediator 0.2 mM, sodium acetate 100 mM and enzyme 0.1 mg EP/mL. In control reactions the enzyme volume was substituted an equivalent amount of $H_2O$. The reactions were incubate 24 hours at 37° C. before being terminated by adding 600 microL of a 100 microM acetonitrile stop solution. Reactions were stored at −20° C. until chromatographic analysis.

Chromatographic Analysis:

Samples were centrifugated and the supernatant analyzed for zearalenone by HPLC-DAD as described by Smedsgaard (*J. Chromatogr. A*, 1997, 760: 264-270). The DAD scanned from 200-600 nm. Separation was done on a Phenomenex (Torrance, Calif.) Luna C18(2) 10×2 mm ID, 3 micrometer, column 2, using a linear gradient moving form 5% to 100% acetonitrile in 20 min. Residual zearalenone was calculated relative to the control. The results are presented in Tables 1 and 2.

TABLE 1

Residual zearalenone (ZEA) after 24 hours incubation with 3 different laccases and two midiators at pH 4.5.

| Enzyme | Mediator | pH | Residual ZEA (%) |
|---|---|---|---|
| Control | MeS | 4.5 | 100 |
| MtL | MeS | 4.5 | 8.8 |
| PpL | MeS | 4.5 | 4 |
| ScL | MeS | 4.5 | 43.2 |
| Control | PPT | 4.5 | 100 |
| MtL | PPT | 4.5 | 0 |
| PpL | PPT | 4.5 | 0 |
| ScL | PPT | 4.5 | 0 |

TABLE 2

Residual zearalenone (ZEA) after 24 hours incubation with 3 different laccases and two midiators at pH 6.

| Enzyme | Mediator | pH | Residual ZEA (%) |
|---|---|---|---|
| Control | MeS | 6.0 | 100 |
| MtL | MeS | 6.0 | 0 |
| PpL | MeS | 6.0 | 0 |
| ScL | MeS | 6.0 | 0 |
| Control | PPT | 6.0 | 100 |
| MtL | PPT | 6.0 | 0 |
| PpL | PPT | 6.0 | 0 |
| ScL | PPT | 6.0 | 0 |

The invention claimed is:

1. A process for degrading zearalenone comprising treating the zearalenone with a laccase.

2. The process of claim 1, wherein the zearalenone is dihydroxy-4-methyl-3-oxabicyclo[12.4.0]octadeca-12,15,17,19-tetraene-2,8-dione.

3. The process of claim 1, wherein the dosage of the laccase is 0.01-100 mg enzyme protein per kg dry matter.

4. The process of claim 1, wherein the dosage of the laccase is 0.1-10 mg enzyme protein per kg dry matter.

5. The process of claim 1, wherein the dosage of the laccase is 1-5 mg enzyme protein per kg dry matter.

6. The process of claim 1, further comprising treating the zearalenone with a laccase mediator.

7. The process of claim 6, wherein the laccase mediator is methylsyringate or phenothiazine-10-propionic acid.

8. The process of claim 6, wherein the laccase mediator is N-(4-cyanophenyl)acetohydroxamic acid (NCPA), acetosyringone, syringaldehyde, p-coumaric acid, 2,2'-Azinobis(3-ethylbenzthiazoline-6-sulfonate), 1-hydroxybenzotriazole, 2,4-pentanedione, or phenothiazine.

9. The process of claim 2, further comprising treating the zearalenone with a laccase mediator.

10. The process of claim 9, wherein the laccase mediator is methylsyringate or phenothiazine-10-propionic acid.

11. The process of claim 9, wherein the laccase mediator is N-(4-cyanophenyl)acetohydroxamic acid (NCPA), acetosyringone, syringaldehyde, p-coumaric acid, 2,2'-Azinobis(3-ethylbenzthiazoline-6-sulfonate), 1-hydroxybenzotriazole, 2,4-pentanedione, or phenothiazine.

12. The process of claim 1, wherein the laccase has at least 95% sequence identity to SEQ ID NO: 1.

13. The process of claim 1, wherein the laccase has at least 95% sequence identity to SEQ ID NO: 2.

14. The process of claim 1, wherein the laccase has at least 95% sequence identity to SEQ ID NO: 3.

15. The process of claim 1, wherein the zearalenone is in a feed product.

16. The process of claim 15, wherein the feed product is a grain based feed product.

17. The process of claim 15, wherein the feed product comprises one or more selected from the group consisting of corn, wheat, barley, rye, rice, sorghum and millet.

18. The process of claim 15, wherein the feed product is an animal feed composition.

19. The process of claim 15, wherein the feed product is a by-product from a fermentation process.

20. The process of claim 15, wherein the feed product comprises brewers spent grain, distiller's spent grain, distiller's wet grain, and/or distiller's dried grain.

* * * * *